United States Patent [19]

Gold

[11] 4,454,888
[45] Jun. 19, 1984

[54] CARDIAC PACING LEAD WITH CURVE RETAINER

[75] Inventor: Philip Gold, Pompano Beach, Fla.

[73] Assignee: Cordis Corporation, Miami, Fla.

[21] Appl. No.: 309,251

[22] Filed: Oct. 7, 1981

[51] Int. Cl.³ .............................................. A61N 1/00
[52] U.S. Cl. .................................... 128/785; 128/786
[58] Field of Search .............................. 128/783–786, 128/772, 419 P, DIG. 9, 657; 604/95, 282

[56] References Cited

U.S. PATENT DOCUMENTS

| | | | |
|---|---|---|---|
| 1,477,695 | 4/1920 | Dolge et al. | |
| 3,367,339 | 10/1964 | Sessions | 128/418 |
| 3,419,010 | 12/1968 | Williamson | 604/170 X |
| 3,516,412 | 6/1970 | Ackerman | 128/786 |
| 3,547,103 | 12/1970 | Cook | 128/772 |
| 3,625,200 | 8/1969 | Muller | 128/2.05 R |
| 3,729,008 | 12/1970 | Berkovits | 128/418 |
| 3,890,977 | 6/1975 | Wilson | 128/785 X |
| 4,003,369 | 4/1975 | Heilman et al. | 128/2 M |
| 4,080,706 | 11/1976 | Heilman et al. | 29/173 |
| 4,136,703 | 1/1979 | Wittkampf | 128/419 P |
| 4,245,624 | 12/1977 | Komiya | 128/4 |
| 4,257,421 | 1/1979 | Beal | 128/348 |
| 4,285,347 | 8/1981 | Hess | 128/786 X |

*Primary Examiner*—Kyle L. Howell
*Assistant Examiner*—Christine A. Fukushima
*Attorney, Agent, or Firm*—Henry W. Collins; Thomas R. Vigil

[57] ABSTRACT

A cardiac pacer lead which includes an insulated electrical conductor having one end adapted to be electrically connected to a pulse generator and the other end electrically connected to an electrode, and a plurality of tines spaced around the circumference of the insulated electrical conductor and projecting in a direction away from the electrode. A curved, flattened spring is embedded within the insulated electrical conductor in a region on the lead near the electrode to thereby provide a lead of a generally J-shaped configuration. The spring serves to maintain the curved configuration of the lead when the lead is implanted in the heart.

5 Claims, 4 Drawing Figures 4,454,888

CARDIAC PACING LEAD WITH CURVE RETAINER

BACKGROUND OF THE INVENTION

Electrical stimulation of the heart is well known and has been utilized to overcome numerous deficiencies in the natural stimulation of the heart. Such external cardiac stimulation requires a reliable means for connecting electrical signals from a pulse generator, or pacer, to a particular region of the wall of the heart. For example, certain types of cardiac pacing lead are connected to the pacer, extend into the heart and are placed in contact with the inside wall of the right ventricle. These leads normally take the form of long, generally straight, flexible, insulated conductors having one end electrically connected to the pacer and the other end connected to an electrode. The electrode is placed in contact with a wall of the heart.

In order to stimulate the ventricle, the pacing lead is inserted into a blood vessel and is then pushed into the lower chamber of the heart, or ventricle. The end of the lead extends along a generally straight line and the electrode rests against the wall of the ventricular cavity. With this arrangement, there is little likelihood that the lead will fall out of this cavity.

On the other hand, a pacing lead which is used for stimulation of the atrium must be formed into a generally J-shaped configuration so that when the lead is inserted into the blood vessel, the lead may be positioned to curve up into the atrial cavity. Another problem associated with placing a pacing lead in the atrium is caused by the fact that the atrium has relatively smooth wall surfaces. With these smooth surfaces, it is difficult to retain the electrode in a fixed position with respect to the wall of the atrium.

Accordingly, one problem with prior pacing leads is that such devices have not been suitable for pacing the atrium. One technique for forming a pacing lead into a generally curved configuration is disclosed in U.S. Pat. No. 3,729,008, issued on Apr. 24, 1973. With the pacing lead disclosed in that patent, the cross-sectional area of the insulation surrounding the electrical conductor is modified in the region of the curved portion of the lead in order to cause the lead to remain in a curved configuration.

The present invention utilizes a curved, flattened spring which is embedded within the pacing lead for maintaining the lead in a curved configuration without the requirement of increasing the diameter of the lead in the curved region of the lead. The curved, flattened spring also imparts substantial torsional rigidity to the lead.

SUMMARY OF THE INVENTION

In accordance with the present invention, there is provided a cardiac pacer lead comprising an insulated electrical conductor having one end adapted to be electrically connected to a pulse generator and the other end electrically connected to an electrode. The electrode serves the function of contacting body tissue so that signals from the pulse generator may be applied to this tissue. The lead also includes a plurality of flexible tines which extend outwardly from the lead in a direction generally away from the electrode. In addition, the lead is of a J-shaped configuration and is retained in this configuration by a curved, flattened spring which is embedded beneath the surface of the lead.

In a preferred form of the invention, the curved, flattened spring extends throughout the curved region of the lead and serves to impart torsional rigidity to the lead in this curved region. With this construction, a stylet or rigid metal wire, may be passed through a central bore in the lead in order to straighten the lead for insertion through blood vessels and into the heart, and then the stylet may be removed to allow the lead to return to the generally J-shaped configuration so that the electrode may be moved into position against the wall of an upper cavity, or atrium, of the heart. The tines serve to attach to trabeculations within the heart in order to retain the electrode against the wall of the heart.

More specifically, according to the invention there is provided a pacing lead assembly which comprises a pacing lead body having a distal end and a proximal end, an elongate, flexible electrical conductors extending substantially the entire length of said lead body, said conductor being in the form of a coiled conductor having the shape of a coil spring to define a stylet receiving lumen within said coiled conductor and extending throughout the length of said lead body, said coiled conductor having in the curved configuration an outer arcuate periphery and an inner arcuate periphery, an electrode at said distal end of said lead body and being electrically connected to said coiled conductor, a connector terminal at the proximal end of said lead body, said coiled conductor extending to said connector terminal, an elongate, curved, flat spring member which is situated within said lead body distal end portion and which has one end attached to said coiled conductor at a first position near said electrode and the other end attached to said coiled conductor at a second position remote from said first position to thereby cause said coiled conductor to take the form of the curved configuration of said spring member between said first and second positions within said distal end portion near the distal end of said lead body, said lead body including an insulating sheath encapsulating both said flat spring member and said coiled conductor over the entire length of the flat spring member and substantially the entire length of said coiled conductor, said spring member having a pre-set generally semi-circular configuration to thereby cause said lead body and coiled conductor therein to take the form of such semi-circular configuration, and said coiled conductor a lumen being capable of receiving a stylet inserted therein for straightening the portion of said lead body having said spring member therein for insertion of said lead body in a generally straight configuration into a heart chamber after which the stylet can be removed to allow said spring member to reassume said semi-circular configuration to cause said distal end portion of said lead body to reassume the curved generally semi-circular configuration in a heart chamber.

DESCRIPTION OF THE PREFERRED EMBODIMENT

Figure 1:
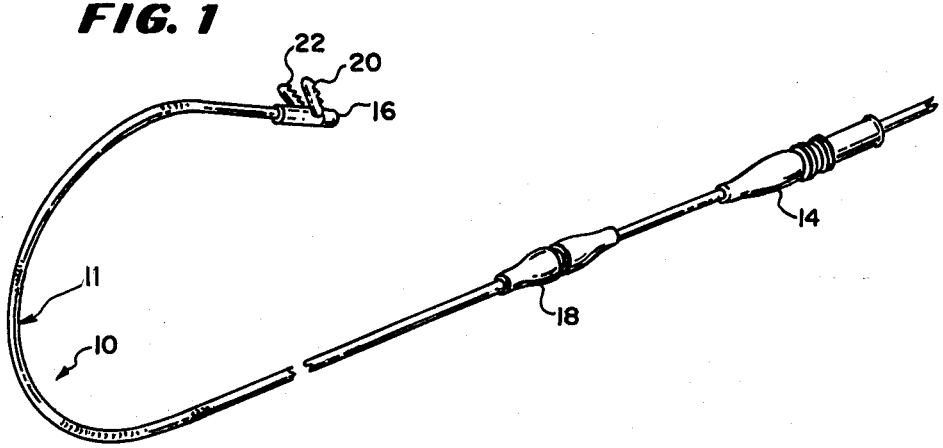
FIG. 1 is a perspective view of a cardiac pacing lead of the present invention.

Referring now to FIG. 1 of the drawings, the cardiac pacing lead assembly 10 of the present invention includes a lead body 11 having an electrical conductor 12 therein with one end connected to a connector terminal 14 and the other end connected to an electrode 16. The connector terminal 14 serves to mechanically and electrically connect the pacing lead assembly 10 to a pulse generator, or pacer. The electrode 16, when positioned in contact with the wall of an organ to be stimulated, such as for example the wall of the atrial cavity, serves to apply the electrical pulses from the pulse generator directly to the wall of the organ.

The pacing lead assembly 10 also includes a suture sleeve 18 which serves to retain the lead body 11 in a fixed position with regard to a blood vessel once the lead body 11 hs been implanted. The lead assembly 10 further includes a pair of rearwardly inclined tines 20, 22, each of which has sawtooth projections extending therefrom, the tines 20 and 22 extending from a sleeve 23 fixed to and extending rearwardly from electrode 16. When the electrode 16 is inserted into the heart, the tines 20, 22 become attached to trabeculations within the heart to thereby cause the electrode 16 to remain in fixed contact with the wall of the heart. The construction of tines 20 form no part of the present invention and are more fully disclosed in co-pending application Ser. No. 311,620 for: Cardiac Pacing Lead With Sawtooth Tines.

Figure 2:
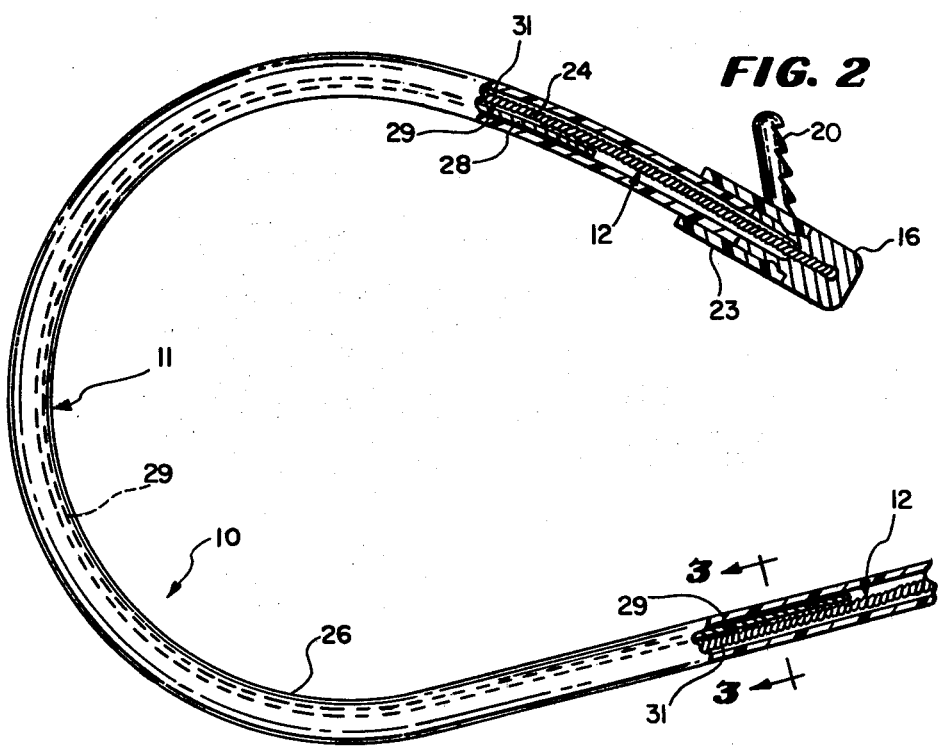
FIG. 2 is a side view of the cardiac pacing lead with portions thereof shown in cross-section in order to illustrate the construction of the curve retainer of the present invention.
Figure 3:
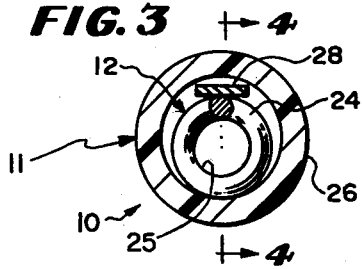
FIG. 3 is a sectional view generally taken along line 3—3 of FIG. 2.
Figure 4:
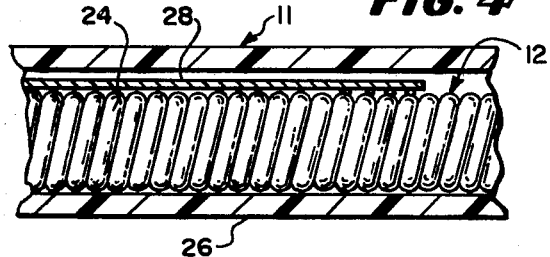
FIG. 4 is an enlarged cross-sectional view of the curved portion of the pacing lead shown in FIG. 2 and is taken along line 4—4 of FIG. 3.

Referring now to FIGS. 2, 3 and 4, the conductor 12 of the cardiac pacing lead assembly 10 preferably includes a coiled conductor 24 which takes the form of a tightly wound coil of wire which extends from the electrode 16 to the connector terminal 14. With this type of construction of the conductor 24, the pacing lead assembly 10 exhibits the property of being very flexible. In addition, a stylet, or relatively rigid straight wire, may be passed through the center or lumen 25 (FIG. 3) of the conductor 24 in order to straighten the lead body 11 during insertion into the heart.

An outer insulative layer or sheath 26 surrounds the conductor 24 over substantially the entire length of the conductor between the electrode 16 and the connector terminal 14.

According to the teachings of the present invention a curved flat spring member 28 is positioned such that the outer flat side of the spring member 28 extends along the conductor from a position near the electrode 16 to a position in the lead body 11 where it is desired to commence the curvature of the curved portion of the body 11. Each end of the flat spring member 28 is then spot welded to several of the turns of the coil conductor 24. With this construction, a region of the conductor 24 near the electrode end of the lead body 11, the distal end portion of the lead body 11, is formed into a generally semi-circular configuration with the flat spring member 28 extending along the inside circumference 29 of the curved coil conductor 24. The curved flat spring member 28 and the conductor 24 are then encased within the insulative layer or sheath 26.

The curved flattened spring member 28 serves to retain the pacing lead body 11 in the curved configuration while also imparting a substantial torsional rigidity to the curved portion of the lead body 11. Accordingly, when it is desired to insert the pacing lead body 11 through a blood vessel into the heart, a stylet, not shown, is passed through the center bore of lumen 25 of the coiled conductor 24 for substantially the entire length of the pacing lead assembly 10. The stylet serves to straighten the curved section of the lead body 11 for insertion into the heart. When the lead body 11 has been inserted into the heart, the stylet is then removed and the flat spring member 28 causes the tip of the lead body 11 to curve back, as illustrated in FIG. 1, in order to place the electrode 16 in contact with the wall of the atrial cavity.

In a preferred embodiment, the curved portion of the lead body 11 has a radius of approximately one inch and is of a general semi-circular configuration.

Modifications can be made to the pacing lead assembly 10 without departing from the teachings of the invention. For example, the flat spring member 28 could be positioned on the other side or outside 31 of the coiled conductor 24 or within the lumen 25 of the coiled conductor 24, or the spring member 28 could be left "free floating" relative to the coiled conductor 24 with the only attachment to the coiled conductor 24 being through the common encasing of these elements.

The present embodiment is therefore to be considered in all respects as illustrative and not restrictive, the scope of the invention being indicated by the appended claims rather than by the foregoing description, and all changes which come within immediate range of the claims, are therefore intended to be embraced therein.

What is claimed is:

1. A pacing lead assembly which comprises:

a pacing lead body having a distal end and a proximal end;

an elongate, flexible electrical conductor extending substantially the entire length of said lead body, said conductor being in the form of a coiled conductor having the shape of a coil spring to define a stylet receiving lumen within said coiled conductor and extending throughout the length of said lead body, sid coiled conductor having in the curved configuration an outer arcuate periphery and an inner arcuate periphery;

an electrode at said distal end of said lead body and being electrically connected to said coiled conductor;

a connector terminal at the proximal end of said lead body, said coiled conductor extending to said connector terminal;

an elongate, curved flat spring member which is situated within said lead body distal end portion and which has one end attached to said coiled conductor at a first position near said electrode and the other end attached to said coiled conductor at a second position remote from said first position to thereby cause said coiled conductor to take the form of the curved configuration of said spring member between said first and second positions within said distal end portion near the distal end of said lead body;

said lead body including an insulating sheat encapsulating both said flat spring member and said coiled conductor over the entire length of the flat spring and substantially the entire length of said coiled conductor, said spring member having a pre-set generally semi-circular configuration to thereby cause said lead body and coiled conductor therein to take the form of said semi-circular configuration, and said coiled conductor lumen being capable of receiving a stylet inserted therein for straightening the portion of said lead body having said spring member therein for insertion of said lead body in a generally straight configuration into a heart chamber after which the stylet can be removed to allow said spring member to reassume said semi-circular configuration to cause said distal end portion of said lead body to reassume the curved generally semi-circular configuration in a heart chamber.

2. The pacing lead assembly of claim 1 including welds fixed to and between said spring member and said coiled conductor at said first and second positions.

3. The pacing lead assembly of claim 1 wherein a flat side of said spring member is positioned adjacent to said conductor on the inside of said semi-circular configuration of said lead body.

4. The pacing lead assembly of claim 2 wherein said spring member is positioned between said sheath and said inner arcuate periphery of said coiled conductor.

5. The pacing lead assembly of claim 1 wherein the distal end of said coiled conductor is electrically connected to said electrode, and the proximal end of said coiled conductor extends to a pacer terminal, and the inner diameter of said coil defines said lumen into which a stylet can be inserted.

* * * * *

UNITED STATES PATENT OFFICE
CERTIFICATE OF CORRECTION

PATENT NO. : 4,454,888
DATED : June 19, 1984
INVENTOR(S) : PHILIP GOLD

It is certified that error appears in the above-identified patent and that said Letters Patent are hereby corrected as shown below:

Column 2, line 49, "coiled conductor alumen" should have been -- coiled conductor lumen --.

Column 3, line 55, "portion of the body" should have been --- portion of the lead body --.

Column 4, line 43, "sid" should have been -- said --.

Column 4, line 62, "sheat" should have been -- sheath --.

Column 6, line 5 "claim 2" should have been -- claim 3 --.

Signed and Sealed this

Seventh Day of May 1985

[SEAL]

Attest:

DONALD J. QUIGG

Attesting Officer　　Acting Commissioner of Patents and Trademarks